United States Patent [19]

Takeuchi et al.

[11] Patent Number: 4,961,874
[45] Date of Patent: Oct. 9, 1990

[54] OPTICALLY ACTIVE TOLAN DERIVATIVES

[75] Inventors: Kiyohumi Takeuchi, Tokyo; Makoto Sasaki, Saitama; Haruyoshi Takatsu, Tokyo, all of Japan

[73] Assignee: Dainippon Ink & Chemicals, Inc., Tokyo, Japan

[21] Appl. No.: 269,817

[22] Filed: Nov. 10, 1988

Related U.S. Application Data

[63] Continuation of Ser. No. 61,242, Jun. 15, 1987, Pat. No. 4,814,516.

[30] Foreign Application Priority Data

Jun. 17, 1986 [JP] Japan .................................. 61-139276
Aug. 13, 1986 [JP] Japan .................................. 61-190053

[51] Int. Cl.$^5$ ............................................. C09K 19/06
[52] U.S. Cl. ............................ 252/299.6; 350/350 S; 350/350 R
[58] Field of Search ..................... 252/299.01, 299.6; 350/350 R, 350 S; 568/646, 631

[56] References Cited

U.S. PATENT DOCUMENTS

| | | | |
|---|---|---|---|
| 3,925,482 | 12/1975 | Jacques | 252/299.6 |
| 4,670,182 | 6/1987 | Fujita et al. | 252/299.6 |
| 4,726,910 | 2/1988 | Takatsu et al. | 252/299.6 |
| 4,728,458 | 3/1958 | Higuchi et al. | 252/299.6 |
| 4,754,051 | 6/1988 | Sasaki et al. | 252/299.6 |
| 4,764,636 | 8/1988 | Sasaki et al. | 560/102 |

OTHER PUBLICATIONS

Malthete et al., Mol. Cryst. Liq. Cryst., vol. 23, pp. 233–260 (1973).
Bernotas et al., Advances in LC Research & Appl., vol. 2, pp. 1019–1022 (1980).

*Primary Examiner*—Matthew A. Thexton
*Assistant Examiner*—Richard Treanor
*Attorney, Agent, or Firm*—Armstrong, Nikaido, Marmelstein, Kubovcik & Murray

[57] ABSTRACT

Novel optically active tolan derivative represented by the general formula (I) and process for preparing thereof;

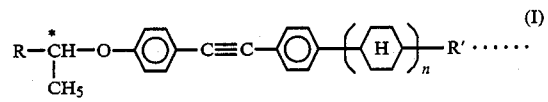

(wherein all the symbols are the same as defined in the appended claims) are disclosed. These are effective for use in preparation of liquid crystal material capable of effectively preventing the formation of the cross-talk phenomenon due to changes due to temperature in the high level multiplexing driving system.

2 Claims, 2 Drawing Sheets

OPTICALLY ACTIVE TOLAN DERIVATIVES

This is a continuation of application Ser. No. 061,242 filed Jun. 15, 1987 now U.S. Pat. No. 4,814,516, 3/21/84.

BACKGROUND OF THE INVENTION

1. Field of the Invention

This invention relates to novel optically active tolan derivatives which are useful as electrooptical display materials.

2. Description of Prior Art

In recent years, liquid crystal display cells of high multiplexing driving systems have been gradually increased in size, leading to an increasing demand as displays for computer terminals, TV sets and so forth. With this increase in demand, liquid crystal materials having high level multiplexibility have been more needed.

High level multiplexing driving systems are depending on change in the environmental temperature and the cross-talk phenomenon will easily occur. In order to prevent the formation of the cross-talk phenomenon due to changes in the environmental temperature, the following have been known; (1) a method in which a temperature compensation circuit is provide in the liquid crystal display equipment, and (2) a method in which the temperature dependency of threshold voltage of liquid crystal material is decreased by adding a chiral substance the molecular orientation of which is twisted right and a chiral substance the molecular orientation of which is twisted left, with respect to the liquid crystal material. The method (1), however, has a disadvantage in that the equipment becomes expensive. Also the method (2) has a disadvantage in that the amount of the substances added is limited because if the amount of the substances added is increased, the response time is decreased, although the substances are necessary to add in large amounts in order to sufficiently obtain the desired effect; therefore the desired effect cannot be obtained sufficiently.

SUMMARY OF THE INVENTION

An object of this invention is to efficiently prevent the cross-talk phenomenon due to changes in the environmental temperature in high level multiplexing driving systems.

Another object of this invention is to provide novel tolan derivatives which when added to various practical nematic liquid crystal compositions, are able to sufficiently decrease the temperature dependency of threshold voltage of the compositions even in small amounts.

It has been found that the objects can be attained by using compounds represented by the general formula (I) as described hereinafter.

This invention provides novel optically active tolan derivatives represented by the general formula (I):

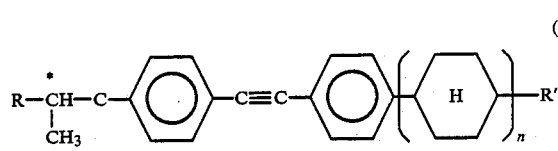
(I)

(wherein R represents a straight alkyl group having 2 to 8 carbon atoms, R' represents a straight alkyl group having 1 to 20 carbon atoms or a straight alkoxy group having 1 to 20 carbon atoms, n represents 0 or 1,

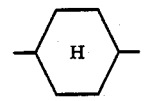

represents a trans(equatorial-equatorial) cyclohexyl ring, and $\overset{*}{C}$ represents an asymmetrical carbon atom).

DETAILED DESCRIPTION OF THE INVENTION

Figure 1:
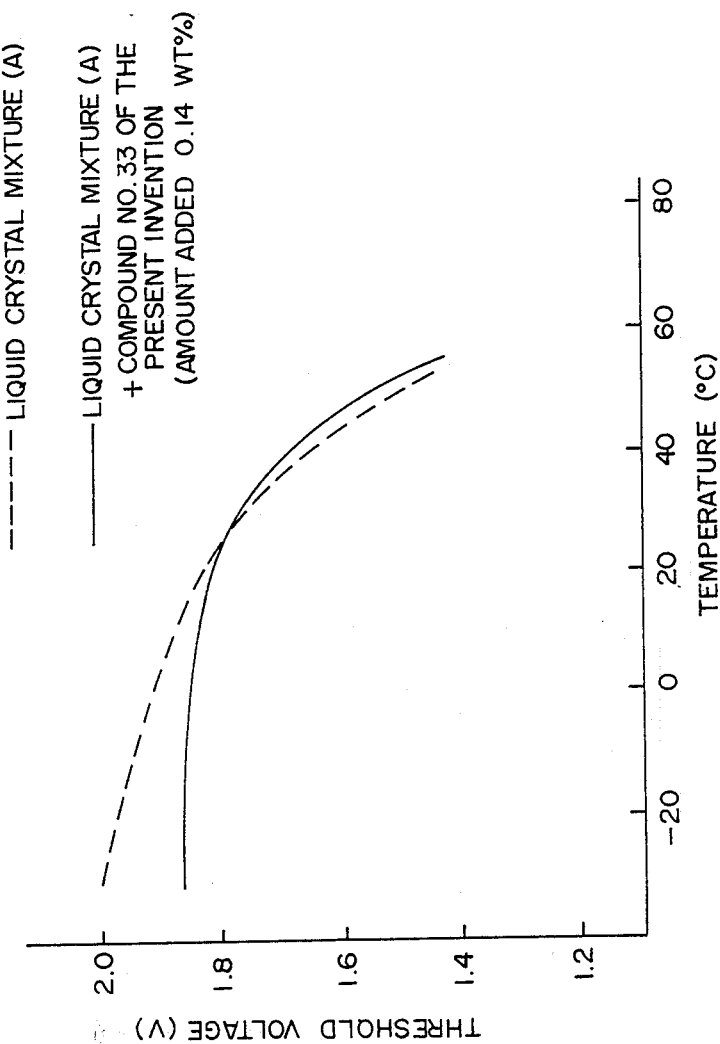
FIG. 1 is a graph showing the temperature dependency of threshold voltage of a chiral nematic liquid crystal composition which is prepared by adding 0.14 wt % of Optically Active Compound No. 33 (dextro rotation:) of the present invention to a mixed liquid crystal (A) commonly used as a nematic liquid crystal material at the present time.

The compounds of the general formula (I) can be prepared according to the following sequence.

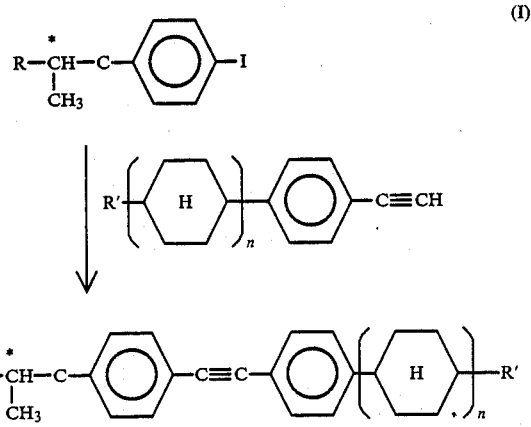

(wherein R, R', n and $\overset{*}{C}$ are as defined above).

4-iodophenyl-1'-methylalkyl ether is reacted with 4-alkylphenylacetylene, 4-alkoxyphenylacetylene, 4-(trans-4'-alkylcyclohexyl)phenylacetylene or 4-(trans- 4'-alkoxycyclohexyl)phenylacetylene in a solvent such as diethylamine by the use of a catalyst such as bis(triphenylphosphine)palladium (II) chloride to form the compound of the general formula (I).

Representative examples of the compounds represented by the general formula (I) are shown in Tables 1 and 2.

TABLE 1

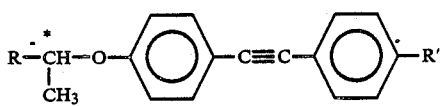

| No. | R | R' |
|---|---|---|
| 1 | $C_2H_5-$ | $CH_3-$ |
| 2 | $n-C_3H_7-$ | $CH_3-$ |
| 3 | $n-C_4H_9-$ | $CH_3-$ |
| 4 | $n-C_5H_{11}-$ | $CH_3-$ |
| 5 | $n-C_6H_{13}-$ | $CH_3-$ |
| 6 | $n-C_7H_{15}-$ | $CH_3-$ |
| 7 | $n-C_8H_{17}-$ | $CH_3-$ |
| 8 | $C_2H_5-$ | $C_2H_5-$ |
| 9 | $n-C_3H_7-$ | $C_2H_5-$ |
| 10 | $n-C_4H_9-$ | $C_2H_5-$ |
| 11 | $n-C_5H_{11}-$ | $C_2H_5-$ |
| 12 | $n-C_6H_{13}-$ | $C_2H_5-$ |
| 13 | $n-C_7H_{15}-$ | $C_2H_5-$ |
| 14 | $n-C_8H_{17}-$ | $C_2H_5-$ |
| 15 | $C_2H_5-$ | $n-C_3H_7-$ |
| 16 | $n-C_3H_7-$ | $n-C_3H_7-$ |
| 17 | $n-C_4H_9-$ | $n-C_3H_7-$ |
| 18 | $n-C_5H_{11}-$ | $n-C_3H_7-$ |
| 19 | $n-C_6H_{13}-$ | $n-C_3H_7-$ |
| 20 | $n-C_7H_{15}-$ | $n-C_3H_7-$ |
| 21 | $n-C_8H_{17}-$ | $n-C_3H_7-$ |
| 22 | $C_2H_5-$ | $n-C_4H_9-$ |
| 23 | $n-C_3H_7-$ | $n-C_4H_9-$ |
| 24 | $n-C_4H_9-$ | $n-C_4H_9-$ |
| 25 | $n-C_5H_{11}-$ | $n-C_4H_9-$ |
| 26 | $n-C_6H_{13}-$ | $n-C_4H_9-$ |
| 27 | $n-C_7H_{15}-$ | $n-C_4H_9-$ |
| 28 | $n-C_8H_{17}-$ | $n-C_4H_9-$ |
| 29 | $C_2H_5-$ | $n-C_5H_{11}-$ |
| 30 | $n-C_3H_7-$ | $n-C_5H_{11}-$ |
| 31 | $n-C_4H_9-$ | $n-C_5H_{11}-$ |
| 32 | $n-C_5H_{11}-$ | $n-C_5H_{11}-$ |
| 33 | $n-C_6H_{13}-$ | $n-C_5H_{11}-$ |
| 34 | $n-C_7H_{15}-$ | $n-C_5H_{11}-$ |
| 35 | $n-C_8H_{17}-$ | $n-C_5H_{11}-$ |
| 36 | $C_2H_5-$ | $n-C_6H_{13}-$ |
| 37 | $n-C_3H_7-$ | $n-C_6H_{13}-$ |
| 38 | $n-C_4H_9-$ | $n-C_6H_{13}-$ |
| 39 | $n-C_5H_{11}-$ | $n-C_6H_{13}-$ |
| 40 | $n-C_6H_{13}-$ | $n-C_6H_{13}-$ |
| 41 | $n-C_7H_{15}-$ | $n-C_6H_{13}-$ |
| 42 | $n-C_8H_{17}-$ | $n-C_6H_{13}-$ |
| 43 | $C_2H_5-$ | $n-C_7H_{15}-$ |
| 44 | $n-C_3H_7-$ | $n-C_7H_{15}-$ |
| 45 | $n-C_4H_9-$ | $n-C_7H_{15}-$ |
| 46 | $n-C_5H_{11}-$ | $n-C_7H_{15}-$ |
| 47 | $n-C_6H_{13}-$ | $n-C_7H_{15}-$ |
| 48 | $n-C_7H_{15}-$ | $n-C_7H_{15}-$ |
| 49 | $n-C_8H_{17}-$ | $n-C_7H_{15}-$ |
| 50 | $C_2H_5-$ | $n-C_8H_{17}-$ |
| 51 | $n-C_3H_7-$ | $n-C_8H_{17}-$ |
| 52 | $n-C_4H_9-$ | $n-C_8H_{17}-$ |
| 53 | $n-C_5H_{11}-$ | $n-C_8H_{17}-$ |

TABLE 1-continued

| No. | R | R' |
|---|---|---|
| 54 | $n-C_6H_{13}-$ | $n-C_8H_{17}-$ |
| 55 | $n-C_7H_{15}-$ | $n-C_8H_{17}-$ |
| 56 | $n-C_8H_{17}-$ | $n-C_8H_{17}-$ |
| 57 | $C_2H_5-$ | $n-C_9H_{19}-$ |
| 58 | $n-C_3H_7-$ | $n-C_9H_{19}-$ |
| 59 | $n-C_4H_9-$ | $n-C_9H_{19}-$ |
| 60 | $n-C_5H_{11}-$ | $n-C_9H_{19}-$ |
| 61 | $n-C_6H_{13}-$ | $n-C_9H_{19}-$ |
| 62 | $n-C_7H_{15}-$ | $n-C_9H_{19}-$ |
| 63 | $n-C_8H_{17}-$ | $n-C_9H_{19}-$ |
| 64 | $C_2H_5-$ | $n-C_{10}H_{21}-$ |
| 65 | $n-C_3H_7-$ | $n-C_{10}H_{21}-$ |
| 66 | $n-C_4H_9-$ | $n-C_{10}H_{21}-$ |
| 67 | $n-C_5H_{11}-$ | $n-C_{10}H_{21}-$ |
| 68 | $n-C_6H_{13}-$ | $n-C_{10}H_{21}-$ |
| 69 | $n-C_7H_{15}-$ | $n-C_{10}H_{21}-$ |
| 70 | $n-C_8H_{17}-$ | $n-C_{10}H_{21}-$ |
| 71 | $C_2H_5-$ | $n-C_{11}H_{23}-$ |
| 72 | $n-C_3H_7-$ | $n-C_{11}H_{23}-$ |
| 73 | $n-C_4H_9-$ | $n-C_{11}H_{23}-$ |
| 74 | $n-C_5H_{11}-$ | $n-C_{11}H_{23}-$ |
| 75 | $n-C_6H_{13}-$ | $n-C_{11}H_{23}-$ |
| 76 | $n-C_7H_{15}-$ | $n-C_{11}H_{23}-$ |
| 77 | $n-C_8H_{17}-$ | $n-C_{11}H_{23}-$ |
| 78 | $C_2H_5-$ | $n-C_{12}H_{25}-$ |
| 79 | $n-C_3H_7-$ | $n-C_{12}H_{25}-$ |
| 80 | $n-C_4H_9-$ | $n-C_{12}H_{25}-$ |
| 81 | $n-C_5H_{11}-$ | $n-C_{12}H_{25}-$ |
| 82 | $n-C_6H_{13}-$ | $n-C_{12}H_{25}-$ |
| 83 | $n-C_7H_{15}-$ | $n-C_{12}H_{25}-$ |
| 84 | $n-C_8H_{17}-$ | $n-C_{12}H_{25}-$ |
| 85 | $C_2H_5-$ | $n-C_{13}H_{27}-$ |
| 86 | $n-C_3H_7-$ | $n-C_{13}H_{27}-$ |
| 87 | $n-C_4H_9-$ | $n-C_{13}H_{27}-$ |
| 88 | $n-C_5H_{11}-$ | $n-C_{13}H_{27}-$ |
| 89 | $n-C_6H_{13}-$ | $n-C_{13}H_{27}-$ |
| 90 | $n-C_7H_{15}-$ | $n-C_{13}H_{27}-$ |
| 91 | $n-C_8H_{17}-$ | $n-C_{13}H_{17}-$ |
| 92 | $C_2H_5-$ | $n-C_{14}H_{29}-$ |
| 93 | $n-C_3H_7-$ | $n-C_{14}H_{29}-$ |
| 94 | $n-C_4H_9-$ | $n-C_{14}H_{29}-$ |
| 95 | $n-C_5H_{11}-$ | $n-C_{14}H_{29}-$ |
| 96 | $n-C_6H_{13}-$ | $n-C_{14}H_{29}-$ |
| 97 | $n-C_7H_{15}-$ | $n-C_{14}H_{29}-$ |
| 98 | $n-C_8H_{17}-$ | $n-C_{14}H_{29}-$ |
| 99 | $C_2H_5-$ | $n-C_{15}H_{31}-$ |
| 100 | $n-C_3H_7-$ | $n-C_{15}H_{31}-$ |
| 101 | $n-C_4H_9-$ | $n-C_{15}H_{31}-$ |
| 102 | $n-C_5H_{11}-$ | $n-C_{15}H_{31}-$ |
| 103 | $n-C_6H_{13}-$ | $n-C_{15}H_{31}-$ |
| 104 | $n-C_7H_{15}-$ | $n-C_{15}H_{31}-$ |
| 105 | $n-C_8H_{17}-$ | $n-C_{15}H_{31}-$ |
| 106 | $C_2H_5-$ | $n-C_{16}H_{33}-$ |
| 107 | $n-C_3H_7-$ | $n-C_{16}H_{33}-$ |
| 108 | $n-C_4H_9-$ | $n-C_{16}H_{33}-$ |
| 109 | $n-C_5H_{11}-$ | $n-C_{16}H_{33}-$ |
| 110 | $n-C_6H_{13}-$ | $n-C_{16}H_{33}-$ |
| 111 | $n-C_7H_{15}-$ | $n-C_{16}H_{33}-$ |
| 112 | $n-C_8H_{17}-$ | $n-C_{16}H_{33}-$ |
| 113 | $C_2H_5-$ | $n-C_{17}H_{35}-$ |
| 114 | $n-C_3H_7-$ | $n-C_{17}H_{35}-$ |
| 115 | $n-C_4H_9-$ | $n-C_{17}H_{35}-$ |
| 116 | $n-C_5H_{11}-$ | $n-C_{17}H_{35}-$ |
| 117 | $n-C_6H_{13}-$ | $n-C_{17}H_{35}-$ |
| 118 | $n-C_7H_{15}-$ | $n-C_{17}H_{35}-$ |
| 119 | $n-C_8H_{17}$ | $n-C_{17}H_{35}-$ |
| 120 | $C_2H_5-$ | $n-C_{18}H_{37}-$ |
| 121 | $n-C_3H_7-$ | $n-C_{18}H_{37}-$ |
| 122 | $n-C_4H_9-$ | $n-C_{18}H_{37}-$ |
| 123 | $n-C_5H_{11}-$ | $n-C_{18}H_{37}-$ |
| 124 | $n-C_6H_{13}-$ | $n-C_{18}H_{37}-$ |
| 125 | $n-C_7H_{15}-$ | $n-C_{18}H_{37}-$ |
| 126 | $n-C_8H_{17}-$ | $n-C_{18}H_{37}-$ |
| 127 | $C_2H_5-$ | $n-C_{19}H_{39}-$ |
| 128 | $n-C_3H_7-$ | $n-C_{19}H_{39}-$ |

TABLE 1-continued $$R-\overset{*}{\underset{CH_3}{CH}}-O-\text{C}_6\text{H}_4-C\equiv C-\text{C}_6\text{H}_4-R'$$

| No. | R | R' |
|---|---|---|
| 129 | n-C$_4$H$_9$— | n-C$_{19}$H$_{39}$— |
| 130 | n-C$_5$H$_{11}$— | n-C$_{19}$H$_{39}$— |
| 131 | n-C$_6$H$_{13}$— | n-C$_{19}$H$_{39}$— |
| 132 | n-C$_7$H$_{15}$— | n-C$_{19}$H$_{39}$— |
| 133 | n-C$_8$H$_{17}$— | n-C$_{19}$H$_{39}$— |
| 134 | C$_2$H$_5$— | n-C$_{20}$H$_{41}$— |
| 135 | n-C$_3$H$_7$— | n-C$_{20}$H$_{41}$— |
| 136 | n-C$_4$H$_9$— | n-C$_{20}$H$_{41}$— |
| 137 | n-C$_5$H$_{11}$— | n-C$_{20}$H$_{41}$— |
| 138 | n-C$_6$H$_{13}$— | n-C$_{20}$H$_{41}$— |
| 139 | n-C$_7$H$_{15}$— | n-C$_{20}$H$_{41}$— |
| 140 | n-C$_8$H$_{17}$— | n-C$_{20}$H$_{41}$— |
| 141 | C$_2$H$_5$— | CH$_3$O— |
| 142 | n-C$_3$H$_7$— | CH$_3$O— |
| 143 | n-C$_4$H$_9$— | CH$_3$O— |
| 144 | n-C$_5$H$_{11}$— | CH$_3$O— |
| 145 | n-C$_6$H$_{13}$— | CH$_3$O— |
| 146 | n-C$_7$H$_{15}$— | CH$_3$O— |
| 147 | n-C$_8$H$_{17}$— | CH$_3$O— |
| 148 | C$_2$H$_5$— | C$_2$H$_5$O— |
| 149 | n-C$_3$H$_7$— | C$_2$H$_5$O— |
| 150 | n-C$_4$H$_9$— | C$_2$H$_5$O— |
| 151 | n-C$_5$H$_{11}$— | C$_2$H$_5$O— |
| 152 | n-C$_6$H$_{13}$— | C$_2$H$_5$O— |
| 153 | n-C$_7$H$_{15}$— | C$_2$H$_5$O— |
| 154 | n-C$_8$H$_{17}$— | C$_2$H$_5$O— |
| 155 | C$_2$H$_5$— | n-C$_3$H$_7$O— |
| 156 | n-C$_3$H$_7$— | n-C$_3$H$_7$O— |
| 157 | n-C$_4$H$_9$— | n-C$_3$H$_7$O— |
| 158 | n-C$_5$H$_{11}$— | n-C$_3$H$_7$O— |
| 159 | n-C$_6$H$_{13}$— | n-C$_3$H$_7$O— |
| 160 | n-C$_7$H$_{15}$— | n-C$_3$H$_7$O— |
| 161 | n-C$_8$H$_{17}$— | n-C$_3$H$_7$O— |
| 162 | C$_2$H$_5$— | n-C$_4$H$_9$O— |
| 163 | n-C$_3$H$_7$— | n-C$_4$H$_9$O— |
| 164 | n-C$_4$H$_9$— | n-C$_4$H$_9$O— |
| 165 | n-C$_5$H$_{11}$— | n-C$_4$H$_9$O— |
| 166 | n-C$_6$H$_{13}$— | n-C$_4$H$_9$O— |
| 167 | n-C$_7$H$_{15}$— | n-C$_4$H$_9$O— |
| 168 | n-C$_8$H$_{17}$— | n-C$_4$H$_9$O— |
| 169 | C$_2$H$_5$— | n-C$_5$H$_{11}$O— |
| 170 | n-C$_3$H$_7$— | n-C$_5$H$_{11}$O— |
| 171 | n-C$_4$H$_9$— | n-C$_5$H$_{11}$O— |
| 172 | n-C$_5$H$_{11}$— | n-C$_5$H$_{11}$O— |
| 173 | n-C$_6$H$_{13}$— | n-C$_5$H$_{11}$O— |
| 174 | n-C$_7$H$_{15}$— | n-C$_5$H$_{11}$O— |
| 175 | n-C$_8$H$_{17}$— | n-C$_5$H$_{11}$O— |
| 176 | C$_2$H$_5$— | n-C$_6$H$_{13}$O— |
| 177 | n-C$_3$H$_7$— | n-C$_6$H$_{13}$O— |
| 178 | n-C$_4$H$_9$— | n-C$_6$H$_{13}$O— |
| 179 | n-C$_5$H$_{11}$— | n-C$_6$H$_{13}$O— |
| 180 | n-C$_6$H$_{13}$— | n-C$_6$H$_{13}$O— |
| 181 | n-C$_7$H$_{15}$— | n-C$_6$H$_{13}$O— |
| 182 | n-C$_8$H$_{17}$— | n-C$_6$H$_{13}$O— |
| 183 | C$_2$H$_5$— | n-C$_7$H$_{15}$O— |
| 184 | n-C$_3$H$_7$— | n-C$_7$H$_{15}$O— |
| 185 | n-C$_4$H$_9$— | n-C$_7$H$_{15}$O— |
| 186 | n-C$_5$H$_{11}$— | n-C$_7$H$_{15}$O— |
| 187 | n-C$_6$H$_{13}$— | n-C$_7$H$_{15}$O— |
| 188 | n-C$_7$H$_{15}$— | n-C$_7$H$_{15}$O— |
| 189 | n-C$_8$H$_{17}$— | n-C$_7$H$_{15}$O— |
| 190 | C$_2$H$_5$— | n-C$_8$H$_{17}$O— |
| 191 | n-C$_3$H$_7$— | n-C$_8$H$_{17}$O— |
| 192 | n-C$_4$H$_9$— | n-C$_8$H$_{17}$O— |
| 193 | n-C$_5$H$_{11}$— | n-C$_8$H$_{17}$O— |
| 194 | n-C$_6$H$_{13}$— | n-C$_8$H$_{17}$O— |
| 195 | n-C$_7$H$_{15}$— | n-C$_8$H$_{17}$O— |
| 196 | n-C$_8$H$_{17}$— | n-C$_8$H$_{17}$O— |
| 197 | C$_2$H$_5$— | n-C$_9$H$_{19}$O— |
| 198 | n-C$_3$H$_7$— | n-C$_9$H$_{19}$O— |
| 199 | n-C$_4$H$_9$— | n-C$_9$H$_{19}$O— |
| 200 | n-C$_5$H$_{11}$— | n-C$_9$H$_{19}$O— |
| 201 | n-C$_6$H$_{13}$— | n-C$_9$H$_{19}$O— |
| 202 | n-C$_7$H$_{15}$— | n-C$_9$H$_{19}$O— |
| 203 | n-C$_8$H$_{17}$— | n-C$_9$H$_{19}$O— |
| 204 | C$_2$H$_5$— | n-C$_{10}$H$_{21}$O— |
| 205 | n-C$_3$H$_7$— | n-C$_{10}$H$_{21}$O— |
| 206 | n-C$_4$H$_9$— | n-C$_{10}$H$_{21}$O— |
| 207 | n-C$_5$H$_{11}$— | n-C$_{10}$H$_{21}$O— |
| 208 | n-C$_6$H$_{13}$— | n-C$_{10}$H$_{21}$O— |
| 209 | n-C$_7$H$_{15}$— | n-C$_{10}$H$_{21}$O— |
| 210 | n-C$_8$H$_{17}$— | n-C$_{10}$H$_{21}$O— |
| 211 | C$_2$H$_5$— | n-C$_{11}$H$_{23}$O— |
| 212 | n-C$_3$H$_7$— | n-C$_{11}$H$_{23}$O— |
| 213 | n-C$_4$H$_9$— | n-C$_{11}$H$_{23}$O— |
| 214 | n-C$_5$H$_{11}$— | n-C$_{11}$H$_{23}$O— |
| 215 | n-C$_6$H$_{13}$— | n-C$_{11}$H$_{23}$O— |
| 216 | n-C$_7$H$_{15}$— | n-C$_{11}$H$_{23}$O— |
| 217 | n-C$_8$H$_{17}$— | n-C$_{11}$H$_{23}$O— |
| 218 | C$_2$H$_5$— | n-C$_{12}$H$_{25}$O— |
| 219 | n-C$_3$H$_7$— | n-C$_{12}$H$_{25}$O— |
| 220 | n-C$_4$H$_9$— | n-C$_{12}$H$_{25}$O— |
| 221 | n-C$_5$H$_{11}$— | n-C$_{12}$H$_{25}$O— |
| 222 | n-C$_6$H$_{13}$— | n-C$_{12}$H$_{25}$O— |
| 223 | n-C$_7$H$_{15}$— | n-C$_{12}$H$_{25}$O— |
| 224 | n-C$_8$H$_{17}$— | n-C$_{12}$H$_{25}$O— |
| 225 | C$_2$H$_5$— | n-C$_{13}$H$_{27}$O— |
| 226 | n-C$_3$H$_7$— | n-C$_{13}$H$_{27}$O— |
| 227 | n-C$_4$H$_9$— | n-C$_{13}$H$_{27}$O— |
| 228 | n-C$_5$H$_{11}$— | n-C$_{13}$H$_{27}$O— |
| 229 | n-C$_6$H$_{13}$— | n-C$_{13}$H$_{27}$O— |
| 230 | n-C$_7$H$_{15}$— | n-C$_{13}$H$_{27}$O— |
| 231 | n-C$_8$H$_{17}$— | n-C$_{13}$H$_{27}$O— |
| 232 | C$_2$H$_5$— | n-C$_{14}$H$_{29}$O— |
| 233 | n-C$_3$H$_7$— | n-C$_{14}$H$_{29}$O— |
| 234 | n-C$_4$H$_9$— | n-C$_{14}$H$_{29}$O— |
| 235 | n-C$_5$H$_{11}$— | n-C$_{14}$H$_{29}$O— |
| 236 | n-C$_6$H$_{13}$— | n-C$_{14}$H$_{29}$O— |
| 237 | n-C$_7$H$_{15}$— | n-C$_{14}$H$_{29}$O— |
| 238 | n-C$_8$H$_{17}$— | n-C$_{14}$H$_{29}$O— |
| 239 | C$_2$H$_5$— | n-C$_{15}$H$_{31}$O— |
| 240 | n-C$_3$H$_7$— | n-C$_{15}$H$_{31}$O— |
| 241 | n-C$_4$H$_9$— | n-C$_{15}$H$_{31}$O— |
| 242 | n-C$_5$H$_{11}$— | n-C$_{15}$H$_{31}$O— |
| 243 | n-C$_6$H$_{13}$— | n-C$_{15}$H$_{31}$O— |
| 244 | n-C$_7$H$_{15}$— | n-C$_{15}$H$_{31}$O— |
| 245 | n-C$_8$H$_{17}$— | n-C$_{15}$H$_{31}$O— |
| 246 | C$_2$H$_5$— | n-C$_{16}$H$_{33}$O— |
| 247 | n-C$_3$H$_7$— | n-C$_{16}$H$_{33}$O— |
| 248 | n-C$_4$H$_9$— | n-C$_{16}$H$_{33}$O— |
| 249 | n-C$_5$H$_{11}$— | n-C$_{16}$H$_{33}$O— |
| 250 | n-C$_6$H$_{13}$— | n-C$_{16}$H$_{33}$O— |
| 251 | n-C$_7$H$_{15}$— | n-C$_{16}$H$_{33}$O— |
| 252 | n-C$_8$H$_{17}$— | n-C$_{16}$H$_{33}$O— |
| 253 | C$_2$H$_5$— | n-C$_{17}$H$_{35}$O— |
| 254 | n-C$_3$H$_7$— | n-C$_{17}$H$_{35}$O— |
| 255 | n-C$_4$H$_9$— | n-C$_{17}$H$_{35}$O— |
| 256 | n-C$_5$H$_{11}$— | n-C$_{17}$H$_{35}$O— |
| 257 | n-C$_6$H$_{13}$— | n-C$_{17}$H$_{35}$O— |
| 258 | n-C$_7$H$_{15}$— | n-C$_{17}$H$_{35}$O— |
| 259 | n-C$_8$H$_{17}$— | n-C$_{17}$H$_{35}$O— |
| 260 | C$_2$H$_5$— | n-C$_{18}$H$_{37}$O— |
| 261 | n-C$_3$H$_7$— | n-C$_{18}$H$_{37}$O— |
| 262 | n-C$_4$H$_9$— | n-C$_{18}$H$_{37}$O— |
| 263 | n-C$_5$H$_{11}$— | n-C$_{18}$H$_{37}$O— |
| 264 | n-C$_6$H$_{13}$— | n-C$_{18}$H$_{37}$O— |
| 265 | n-C$_7$H$_{15}$— | n-C$_{18}$H$_{37}$O— |
| 266 | n-C$_8$H$_{17}$— | n-C$_{18}$H$_{37}$O— |
| 267 | C$_2$H$_5$— | n-C$_{19}$H$_{39}$O— |
| 268 | n-C$_3$H$_7$— | n-C$_{19}$H$_{39}$O— |
| 269 | n-C$_4$H$_9$— | n-C$_{19}$H$_{39}$O— |
| 270 | n-C$_5$H$_{11}$— | n-C$_{19}$H$_{39}$O— |
| 271 | n-C$_6$H$_{13}$— | n-C$_{19}$H$_{39}$O— |
| 272 | n-C$_7$H$_{15}$— | n-C$_{19}$H$_{39}$O— |
| 273 | n-C$_8$H$_{17}$— | n-C$_{19}$H$_{39}$O— |
| 274 | C$_2$H$_5$— | n-C$_{20}$H$_{41}$O— |
| 275 | n-C$_3$H$_7$— | n-C$_{20}$H$_{41}$O— |
| 276 | n-C$_4$H$_9$— | n-C$_{20}$H$_{41}$O— |
| 277 | n-C$_5$H$_{11}$— | n-C$_{20}$H$_{41}$O— |
| 278 | n-C$_6$H$_{13}$— | n-C$_{20}$H$_{41}$O— |

TABLE 1-continued

R—*CH(CH₃)—O—⟨phenyl⟩—C≡C—⟨phenyl⟩—R'

| No. | R | R' |
|---|---|---|
| 279 | n-C$_7$H$_{15}$— | n-C$_{20}$H$_{41}$O— |
| 280 | n-C$_8$H$_{17}$— | n-C$_{20}$H$_{41}$O— |

TABLE 2

R—*CH(CH₃)—O—⟨phenyl⟩—C≡C—⟨phenyl⟩—⟨H cyclohexyl⟩—R'

| No. | R | R' |
|---|---|---|
| 281 | C$_2$H$_5$— | CH$_3$— |
| 282 | n-C$_3$H$_7$— | CH$_3$— |
| 283 | n-C$_4$H$_9$— | CH$_3$— |
| 284 | n-C$_5$H$_{11}$— | CH$_3$— |
| 285 | n-C$_6$H$_{13}$— | CH$_3$— |
| 286 | n-C$_7$H$_{15}$— | CH$_3$— |
| 287 | n-C$_8$H$_{17}$— | CH$_3$— |
| 288 | C$_2$H$_5$— | C$_2$H$_5$— |
| 289 | n-C$_3$H$_7$— | C$_2$H$_5$— |
| 290 | n-C$_4$H$_9$— | C$_2$H$_5$— |
| 291 | n-C$_5$H$_{11}$— | C$_2$H$_5$— |
| 292 | n-C$_6$H$_{13}$— | C$_2$H$_5$— |
| 293 | n-C$_7$H$_{15}$— | C$_2$H$_5$— |
| 294 | n-C$_8$H$_{17}$— | C$_2$H$_5$— |
| 295 | C$_2$H$_5$— | n-C$_3$H$_7$— |
| 296 | n-C$_3$H$_7$— | n-C$_3$H$_7$— |
| 297 | n-C$_4$H$_9$— | n-C$_3$H$_7$— |
| 298 | n-C$_5$H$_{11}$— | n-C$_3$H$_7$— |
| 299 | n-C$_6$H$_{13}$— | n-C$_3$H$_7$— |
| 300 | n-C$_7$H$_{15}$— | n-C$_3$H$_7$— |
| 301 | n-C$_8$H$_{17}$— | n-C$_3$H$_7$— |
| 302 | C$_2$H$_5$— | n-C$_4$H$_9$— |
| 303 | n-C$_3$H$_7$— | n-C$_4$H$_9$— |
| 304 | n-C$_4$H$_9$— | n-C$_4$H$_9$— |
| 305 | n-C$_5$H$_{11}$— | n-C$_4$H$_9$— |
| 306 | n-C$_6$H$_{13}$— | n-C$_4$H$_9$— |
| 307 | n-C$_7$H$_{15}$— | n-C$_4$H$_9$— |
| 308 | n-C$_8$H$_{17}$— | n-C$_4$H$_9$— |
| 309 | C$_2$H$_5$— | n-C$_5$H$_{11}$— |
| 310 | n-C$_3$H$_7$— | n-C$_5$H$_{11}$— |
| 311 | n-C$_4$H$_9$— | n-C$_5$H$_{11}$— |
| 312 | n-C$_5$H$_{11}$— | n-C$_5$H$_{11}$— |
| 313 | n-C$_6$H$_{13}$— | n-C$_5$H$_{11}$— |
| 314 | n-C$_7$H$_{15}$— | n-C$_5$H$_{11}$— |
| 315 | n-C$_8$H$_{17}$— | n-C$_5$H$_{11}$— |
| 316 | C$_2$H$_5$— | n-C$_6$H$_{13}$— |
| 317 | n-C$_3$H$_7$— | n-C$_6$H$_{13}$— |
| 318 | n-C$_4$H$_9$— | n-C$_6$H$_{13}$— |
| 319 | n-C$_5$H$_{11}$— | n-C$_6$H$_{13}$— |
| 320 | n-C$_6$H$_{13}$— | n-C$_6$H$_{13}$— |
| 321 | n-C$_7$H$_{15}$— | n-C$_6$H$_{13}$— |
| 322 | n-C$_8$H$_{17}$— | n-C$_6$H$_{13}$— |
| 323 | C$_2$H$_5$— | n-C$_7$H$_{15}$— |
| 324 | n-C$_3$H$_7$— | n-C$_7$H$_{15}$— |
| 325 | n-C$_4$H$_9$— | n-C$_7$H$_{15}$— |
| 326 | n-C$_5$H$_{11}$— | n-C$_7$H$_{15}$— |
| 327 | n-C$_6$H$_{13}$— | n-C$_7$H$_{15}$— |
| 328 | n-C$_7$H$_{15}$— | n-C$_7$H$_{15}$— |
| 329 | n-C$_8$H$_{17}$— | n-C$_7$H$_{15}$— |
| 330 | C$_2$H$_5$— | n-C$_8$H$_{17}$— |
| 331 | n-C$_3$H$_7$— | n-C$_8$H$_{17}$— |
| 332 | n-C$_4$H$_9$— | n-C$_8$H$_{17}$— |
| 333 | n-C$_5$H$_{11}$— | n-C$_8$H$_{17}$— |
| 334 | n-C$_6$H$_{13}$— | n-C$_8$H$_{17}$— |
| 335 | n-C$_7$H$_{15}$— | n-C$_8$H$_{17}$— |
| 336 | n-C$_8$H$_{17}$— | n-C$_8$H$_{17}$— |
| 337 | C$_2$H$_5$— | n-C$_9$H$_{19}$— |
| 338 | n-C$_3$H$_7$— | n-C$_9$H$_{19}$— |
| 339 | n-C$_4$H$_9$— | n-C$_9$H$_{19}$— |
| 340 | n-C$_5$H$_{11}$— | n-C$_9$H$_{19}$— |
| 341 | n-C$_6$H$_{13}$— | n-C$_9$H$_{19}$— |
| 342 | n-C$_7$H$_{15}$— | n-C$_9$H$_{19}$— |
| 343 | n-C$_8$H$_{17}$— | n-C$_9$H$_{19}$— |
| 344 | C$_2$H$_5$— | n-C$_{10}$H$_{21}$— |
| 345 | n-C$_3$H$_7$— | n-C$_{10}$H$_{21}$— |
| 346 | n-C$_4$H$_9$— | n-C$_{10}$H$_{21}$— |
| 347 | n-C$_5$H$_{11}$— | n-C$_{10}$H$_{21}$— |
| 348 | n-C$_6$H$_{13}$— | n-C$_{10}$H$_{21}$— |
| 349 | n-C$_7$H$_{15}$— | n-C$_{10}$H$_{21}$— |
| 350 | n-C$_8$H$_{17}$— | n-C$_{10}$H$_{21}$— |
| 351 | C$_2$H$_5$— | n-C$_{11}$H$_{23}$— |
| 352 | n-C$_3$H$_7$— | n-C$_{11}$H$_{23}$— |
| 353 | n-C$_4$H$_9$— | n-C$_{11}$H$_{23}$— |
| 354 | n-C$_5$H$_{11}$— | n-C$_{11}$H$_{23}$— |
| 355 | n-C$_6$H$_{13}$— | n-C$_{11}$H$_{23}$— |
| 356 | n-C$_7$H$_{15}$— | n-C$_{11}$H$_{23}$— |
| 357 | n-C$_8$H$_{17}$— | n-C$_{11}$H$_{23}$— |
| 358 | C$_2$H$_5$— | n-C$_{12}$H$_{25}$— |
| 359 | n-C$_3$H$_7$— | n-C$_{12}$H$_{25}$— |
| 360 | n-C$_4$H$_9$— | n-C$_{12}$H$_{25}$— |
| 361 | n-C$_5$H$_{11}$— | n-C$_{12}$H$_{25}$— |
| 362 | n-C$_6$H$_{13}$— | n-C$_{12}$H$_{25}$— |
| 363 | n-C$_7$H$_{15}$— | n-C$_{12}$H$_{25}$— |
| 364 | n-C$_8$H$_{17}$— | n-C$_{12}$H$_{25}$— |
| 365 | C$_2$H$_5$— | n-C$_{13}$H$_{27}$— |
| 366 | n-C$_3$H$_7$— | n-C$_{13}$H$_{27}$— |
| 367 | n-C$_4$H$_9$— | n-C$_{13}$H$_{27}$— |
| 368 | n-C$_5$H$_{11}$— | n-C$_{13}$H$_{27}$— |
| 369 | n-C$_6$H$_{13}$— | n-C$_{13}$H$_{27}$— |
| 370 | n-C$_7$H$_{15}$— | n-C$_{13}$H$_{27}$— |
| 371 | n-C$_8$H$_{17}$— | n-C$_{13}$H$_{27}$— |
| 372 | C$_2$H$_5$— | n-C$_{14}$H$_{29}$— |
| 373 | n-C$_3$H$_7$— | n-C$_{14}$H$_{29}$— |
| 374 | n-C$_4$H$_9$— | n-C$_{14}$H$_{29}$— |
| 375 | n-C$_5$H$_{11}$— | n-C$_{14}$H$_{29}$— |
| 376 | n-C$_6$H$_{13}$— | n-C$_{14}$H$_{29}$— |
| 377 | n-C$_7$H$_{15}$— | n-C$_{14}$H$_{29}$— |
| 378 | n-C$_8$H$_{17}$— | n-C$_{14}$H$_{29}$— |
| 379 | C$_2$H$_5$— | n-C$_{15}$H$_{31}$— |
| 380 | n-C$_3$H$_7$— | n-C$_{15}$H$_{31}$— |
| 381 | n-C$_4$H$_9$— | n-C$_{15}$H$_{31}$— |
| 382 | n-C$_5$H$_{11}$— | n-C$_{15}$H$_{31}$— |
| 383 | n-C$_6$H$_{13}$— | n-C$_{15}$H$_{31}$— |
| 384 | n-C$_7$H$_{15}$— | n-C$_{15}$H$_{31}$— |
| 385 | n-C$_8$H$_{17}$— | n-C$_{15}$H$_{31}$— |
| 386 | C$_2$H$_5$— | n-C$_{16}$H$_{33}$— |
| 387 | n-C$_3$H$_7$— | n-C$_{16}$H$_{33}$— |
| 388 | n-C$_4$H$_9$— | n-C$_{16}$H$_{33}$— |
| 389 | n-C$_5$H$_{11}$— | n-C$_{16}$H$_{33}$— |
| 390 | n-C$_6$H$_{13}$— | n-C$_{16}$H$_{33}$— |
| 391 | n-C$_7$H$_{15}$— | n-C$_{16}$H$_{33}$— |
| 392 | n-C$_8$H$_{17}$— | n-C$_{16}$H$_{33}$— |
| 393 | C$_2$H$_5$— | n-C$_{17}$H$_{35}$— |
| 394 | n-C$_3$H$_7$— | n-C$_{17}$H$_{35}$— |
| 395 | n-C$_4$H$_9$— | n-C$_{17}$H$_{35}$— |
| 396 | n-C$_5$H$_{11}$— | n-C$_{17}$H$_{35}$— |
| 397 | n-C$_6$H$_{13}$— | n-C$_{17}$H$_{35}$— |
| 398 | n-C$_7$H$_{15}$— | n-C$_{17}$H$_{35}$— |
| 399 | n-C$_8$H$_{17}$— | n-C$_{17}$H$_{35}$— |
| 400 | C$_2$H$_5$— | n-C$_{18}$H$_{37}$— |
| 401 | n-C$_3$H$_7$— | n-C$_{18}$H$_{37}$— |
| 402 | n-C$_4$H$_9$— | n-C$_{18}$H$_{37}$— |
| 403 | n-C$_5$H$_{11}$— | n-C$_{18}$H$_{37}$— |
| 404 | n-C$_6$H$_{13}$— | n-C$_{18}$H$_{37}$— |
| 405 | n-C$_7$H$_{15}$— | n-C$_{18}$H$_{37}$— |
| 406 | n-C$_8$H$_{17}$— | n-C$_{18}$H$_{37}$— |

TABLE 2-continued

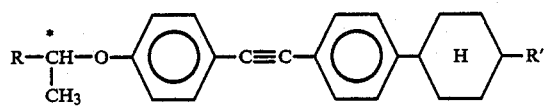

| No. | R | R' |
|---|---|---|
| 407 | $C_2H_5-$ | $n-C_{19}H_{39}-$ |
| 408 | $n-C_3H_7-$ | $n-C_{19}H_{39}-$ |
| 409 | $n-C_4H_9-$ | $n-C_{19}H_{39}-$ |
| 410 | $n-C_5H_{11}-$ | $n-C_{19}H_{39}-$ |
| 411 | $n-C_6H_{13}-$ | $n-C_{19}H_{39}-$ |
| 412 | $n-C_7H_{15}-$ | $n-C_{19}H_{39}-$ |
| 413 | $n-C_8H_{17}-$ | $n-C_{19}H_{39}-$ |
| 414 | $C_2H_5-$ | $n-C_{20}H_{41}-$ |
| 415 | $n-C_3H_7-$ | $n-C_{20}H_{41}-$ |
| 416 | $n-C_4H_9-$ | $n-C_{20}H_{41}-$ |
| 417 | $n-C_5H_{11}-$ | $n-C_{20}H_{41}-$ |
| 418 | $n-C_6H_{13}-$ | $n-C_{20}H_{41}-$ |
| 419 | $n-C_7H_{15}-$ | $n-C_{20}H_{41}-$ |
| 420 | $n-C_8H_{17}-$ | $n-C_{20}H_{41}-$ |
| 421 | $C_2H_5-$ | $CH_3O-$ |
| 422 | $n-C_3H_7-$ | $CH_3O-$ |
| 423 | $n-C_4H_9-$ | $CH_3O-$ |
| 424 | $n-C_5H_{11}-$ | $CH_3O-$ |
| 425 | $n-C_6H_{13}-$ | $CH_3O-$ |
| 426 | $n-C_7H_{15}-$ | $CH_3O-$ |
| 427 | $n-C_8H_{17}-$ | $CH_3O-$ |
| 428 | $C_2H_5-$ | $C_2H_5O-$ |
| 429 | $n-C_3H_7-$ | $C_2H_5O-$ |
| 430 | $n-C_4H_9-$ | $C_2H_5O-$ |
| 431 | $n-C_5H_{11}-$ | $C_2H_5O-$ |
| 432 | $n-C_6H_{13}-$ | $C_2H_5O-$ |
| 433 | $n-C_7H_{15}-$ | $C_2H_5O-$ |
| 434 | $n-C_8H_{17}-$ | $C_2H_5O-$ |
| 435 | $C_2H_5-$ | $n-C_3H_7O-$ |
| 436 | $n-C_3H_7-$ | $n-C_3H_7O-$ |
| 437 | $n-C_4H_9-$ | $n-C_3H_7O-$ |
| 438 | $n-C_5H_{11}-$ | $n-C_3H_7O-$ |
| 439 | $n-C_6H_{13}-$ | $n-C_3H_7O-$ |
| 440 | $n-C_7H_{15}-$ | $n-C_3H_7O-$ |
| 441 | $n-C_8H_{17}-$ | $n-C_3H_7O-$ |
| 442 | $C_2H_5-$ | $n-C_4H_9O-$ |
| 443 | $n-C_3H_7-$ | $n-C_4H_9O-$ |
| 444 | $n-C_4H_9-$ | $n-C_4H_9O-$ |
| 445 | $n-C_5H_{11}-$ | $n-C_4H_9O-$ |
| 446 | $n-C_6H_{13}-$ | $n-C_4H_9O-$ |
| 447 | $n-C_7H_{15}-$ | $n-C_4H_9O-$ |
| 448 | $n-C_8H_{17}-$ | $n-C_4H_9O-$ |
| 449 | $C_2H_5-$ | $n-C_5H_{11}O-$ |
| 450 | $n-C_3H_7-$ | $n-C_5H_{11}O-$ |
| 451 | $n-C_4H_9-$ | $n-C_5H_{11}O-$ |
| 452 | $n-C_5H_{11}-$ | $n-C_5H_{11}O-$ |
| 453 | $n-C_6H_{13}-$ | $n-C_5H_{11}O-$ |
| 454 | $n-C_7H_{15}-$ | $n-C_5H_{11}O-$ |
| 455 | $n-C_8H_{17}-$ | $n-C_5H_{11}O-$ |
| 456 | $C_2H_5-$ | $n-C_6H_{13}O-$ |
| 457 | $n-C_3H_7-$ | $n-C_6H_{13}O-$ |
| 458 | $n-C_4H_9-$ | $n-C_6H_{13}O-$ |
| 459 | $n-C_5H_{11}-$ | $n-C_6H_{13}O-$ |
| 460 | $n-C_6H_{13}-$ | $n-C_6H_{13}O-$ |
| 461 | $n-C_7H_{15}-$ | $n-C_6H_{13}O-$ |
| 462 | $n-C_8H_{17}-$ | $n-C_6H_{13}O-$ |
| 463 | $C_2H_5-$ | $n-C_7H_{15}O-$ |
| 464 | $n-C_3H_7-$ | $n-C_7H_{15}O-$ |
| 465 | $n-C_4H_9-$ | $n-C_7H_{15}O-$ |
| 466 | $n-C_5H_{11}-$ | $n-C_7H_{15}O-$ |
| 467 | $n-C_6H_{13}-$ | $n-C_7H_{15}O-$ |
| 468 | $n-C_7H_{15}-$ | $n-C_7H_{15}O-$ |
| 469 | $n-C_8H_{17}-$ | $n-C_7H_{15}O-$ |
| 470 | $C_2H_5-$ | $n-C_8H_{17}O-$ |
| 471 | $n-C_3H_7-$ | $n-C_8H_{17}O-$ |
| 472 | $n-C_4H_9-$ | $n-C_8H_{17}O-$ |
| 473 | $n-C_5H_{11}-$ | $n-C_8H_{17}O-$ |
| 474 | $n-C_6H_{13}-$ | $n-C_8H_{17}O-$ |
| 475 | $n-C_7H_{15}-$ | $n-C_8H_{17}O-$ |
| 476 | $n-C_8H_{17}-$ | $n-C_8H_{17}O-$ |
| 477 | $C_2H_5-$ | $n-C_9H_{19}O-$ |
| 478 | $n-C_3H_7-$ | $n-C_9H_{19}O-$ |
| 479 | $n-C_4H_9-$ | $n-C_9H_{19}O-$ |
| 480 | $n-C_5H_{11}-$ | $n-C_9H_{19}O-$ |
| 481 | $n-C_6H_{13}-$ | $n-C_9H_{19}O-$ |

TABLE 2-continued

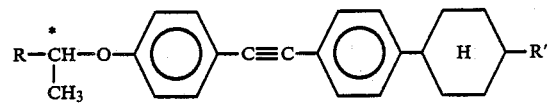

| No. | R | R' |
|---|---|---|
| 482 | $n-C_7H_{15}-$ | $n-C_9H_{19}O-$ |
| 483 | $n-C_8H_{17}-$ | $n-C_9H_{19}O-$ |
| 484 | $C_2H_5-$ | $n-C_{10}H_{21}O-$ |
| 485 | $n-C_3H_7-$ | $n-C_{10}H_{21}O-$ |
| 486 | $n-C_4H_9-$ | $n-C_{10}H_{21}O-$ |
| 487 | $n-C_5H_{11}-$ | $n-C_{10}H_{21}O-$ |
| 488 | $n-C_6H_{13}-$ | $n-C_{10}H_{21}O-$ |
| 489 | $n-C_7H_{15}-$ | $n-C_{10}H_{21}O-$ |
| 490 | $n-C_8H_{17}-$ | $n-C_{10}H_{21}O-$ |
| 491 | $C_2H_5-$ | $n-C_{11}H_{23}O-$ |
| 492 | $n-C_3H_7-$ | $n-C_{11}H_{23}O-$ |
| 493 | $n-C_4H_9-$ | $n-C_{11}H_{23}O-$ |
| 494 | $n-C_5H_{11}-$ | $n-C_{11}H_{23}O-$ |
| 495 | $n-C_6H_{13}-$ | $n-C_{11}H_{23}O-$ |
| 496 | $n-C_7H_{15}-$ | $n-C_{11}H_{23}O-$ |
| 497 | $n-C_8H_{17}-$ | $n-C_{11}H_{23}O-$ |
| 498 | $C_2H_5-$ | $n-C_{12}H_{25}O-$ |
| 499 | $n-C_3H_7-$ | $n-C_{12}H_{25}O-$ |
| 500 | $n-C_4H_9-$ | $n-C_{12}H_{25}O-$ |
| 501 | $n-C_5H_{11}-$ | $n-C_{12}H_{25}O-$ |
| 502 | $n-C_6H_{13}-$ | $n-C_{12}H_{25}O-$ |
| 503 | $n-C_7H_{15}-$ | $n-C_{12}H_{25}O-$ |
| 504 | $n-C_8H_{17}-$ | $n-C_{12}H_{25}O-$ |
| 505 | $C_2H_5-$ | $n-C_{13}H_{27}O-$ |
| 506 | $n-C_3H_7-$ | $n-C_{13}H_{27}O-$ |
| 507 | $n-C_4H_9-$ | $n-C_{13}H_{27}O-$ |
| 508 | $n-C_5H_{11}-$ | $n-C_{13}H_{27}O-$ |
| 509 | $n-C_6H_{13}-$ | $n-C_{13}H_{27}O-$ |
| 510 | $n-C_7H_{15}-$ | $n-C_{13}H_{27}O-$ |
| 511 | $n-C_8H_{17}-$ | $n-C_{13}H_{27}O-$ |
| 512 | $C_2H_5-$ | $n-C_{14}H_{29}O-$ |
| 513 | $n-C_3H_7-$ | $n-C_{14}H_{29}O-$ |
| 514 | $n-C_4H_9-$ | $n-C_{14}H_{29}O-$ |
| 515 | $n-C_5H_{11}-$ | $n-C_{14}H_{29}O-$ |
| 516 | $n-C_6H_{13}-$ | $n-C_{14}H_{29}O-$ |
| 517 | $n-C_7H_{15}-$ | $n-C_{14}H_{29}O-$ |
| 518 | $n-C_8H_{17}-$ | $n-C_{14}H_{29}O-$ |
| 519 | $C_2H_5-$ | $n-C_{15}H_{31}O-$ |
| 520 | $n-C_3H_7-$ | $n-C_{15}H_{31}O-$ |
| 521 | $n-C_4H_9-$ | $n-C_{15}H_{31}O-$ |
| 522 | $n-C_5H_{11}-$ | $n-C_{15}H_{31}O-$ |
| 523 | $n-C_6H_{13}-$ | $n-C_{15}H_{31}O-$ |
| 524 | $n-C_7H_{15}-$ | $n-C_{15}H_{31}O-$ |
| 525 | $n-C_8H_{17}-$ | $n-C_{15}H_{31}O-$ |
| 526 | $C_2H_5-$ | $n-C_{16}H_{33}O-$ |
| 527 | $n-C_3H_7-$ | $n-C_{16}H_{33}O-$ |
| 528 | $n-C_4H_9-$ | $n-C_{16}H_{33}O-$ |
| 529 | $n-C_5H_{11}-$ | $n-C_{16}H_{33}O-$ |
| 530 | $n-C_6H_{13}-$ | $n-C_{16}H_{33}O-$ |
| 531 | $n-C_7H_{15}-$ | $n-C_{16}H_{33}O-$ |
| 532 | $n-C_8H_{17}-$ | $n-C_{16}H_{33}O-$ |
| 533 | $C_2H_5-$ | $n-C_{17}H_{35}O-$ |
| 534 | $n-C_3H_7-$ | $n-C_{17}H_{35}O-$ |
| 535 | $n-C_4H_9-$ | $n-C_{17}H_{35}O-$ |
| 536 | $n-C_5H_{11}-$ | $n-C_{17}H_{35}O-$ |
| 537 | $n-C_6H_{13}-$ | $n-C_{17}H_{35}O-$ |
| 538 | $n-C_7H_{15}-$ | $n-C_{17}H_{35}O-$ |
| 539 | $n-C_8H_{17}-$ | $n-C_{17}H_{35}O-$ |
| 540 | $C_2H_5-$ | $n-C_{18}H_{37}O-$ |
| 541 | $n-C_3H_7-$ | $n-C_{18}H_{37}O-$ |
| 542 | $n-C_4H_9-$ | $n-C_{18}H_{37}O-$ |
| 543 | $n-C_5H_{11}-$ | $n-C_{18}H_{37}O-$ |
| 544 | $n-C_6H_{13}-$ | $n-C_{18}H_{37}O-$ |
| 545 | $n-C_7H_{15}-$ | $n-C_{18}H_{37}O-$ |
| 546 | $n-C_8H_{17}-$ | $n-C_{18}H_{37}O-$ |
| 547 | $C_2H_5-$ | $n-C_{19}H_{39}O-$ |
| 548 | $n-C_3H_7-$ | $n-C_{19}H_{39}O-$ |
| 549 | $n-C_4H_9-$ | $n-C_{19}H_{39}O-$ |
| 550 | $n-C_5H_{11}-$ | $n-C_{19}H_{39}O-$ |
| 551 | $n-C_6H_{13}-$ | $n-C_{19}H_{39}O-$ |
| 552 | $n-C_7H_{15}-$ | $n-C_{19}H_{39}O-$ |
| 553 | $n-C_8H_{17}-$ | $n-C_{19}H_{39}O-$ |
| 554 | $C_2H_5-$ | $n-C_{20}H_{41}O-$ |
| 555 | $n-C_3H_7-$ | $n-C_{20}H_{41}O-$ |
| 556 | $n-C_4H_9-$ | $n-C_{20}H_{41}O-$ |

TABLE 2-continued

R—CH(CH₃)—O—⌬—C≡C—⌬—H—R'

| No. | R | R' |
|---|---|---|
| 557 | n-C₅H₁₁— | n-C₂₀H₄₁O— |
| 558 | n-C₆H₁₃— | n-C₂₀H₄₁O— |
| 559 | n-C₇H₁₅— | n-C₂₀H₄₁O— |
| 560 | n-C₈H₁₇— | n-C₂₀H₄₁O— |

In the general formula (I), the sum of the number of carbon atoms contained in the alkyl group represented by R and the number of carbon atoms contained in the alkyl or alkoxy group represented by R' is preferably 3 to 20. Compounds of the general formula (I) wherein n represents 0, R represents a straight alkyl group having 2 to 8 carbon atoms, and R' represents a straight alkyl group having 1 to 12 carbon atoms, or wherein n represents 0, R represents a straight alkyl group having 2 to 8 carbon atoms, and R' represents a straight alkoxy group having 1 to 12 are preferred. In addition, compounds of the general formula (I) wherein n represents 1, R represents a straight alkyl group having 2 to 8 carbon atoms, and R' represents a straight alkyl group having 1 to 12 carbon atoms, or wherein n represents 1, R represents a straight alkyl group having 2 to 8 carbon atoms, and R' represents a straight alkoxy group having 1 to 12 carbon atoms are preferred.

Many nematic liquid crystal compositions commonly used at the present time can be sufficiently decreased in the temperature dependency of threshold voltage by adding the compounds of the general formula (I) of this invention only in small amounts.

FIG. 1 is a graph showing the temperature dependency of threshold voltage of each of a mixed liquid crystal (A) commonly used as a nematic liquid crystal material at the present time and of a chiral nematic liquid crystal composition as prepared by adding 0.14 wt % of Compound No. 33 (dextro rotation) of the present invention to the mixed liquid crystal (A). This chiral nematic liquid crystal composition has a pitch of 200 μm.

The mixed liquid crystal (A) is composed of:

11 wt % of

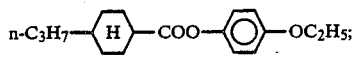
n-C₃H₇—⟨H⟩—COO—⌬—OC₂H₅;

11 wt % of

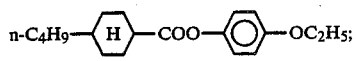
n-C₄H₉—⟨H⟩—COO—⌬—OC₂H₅;

11 wt % of

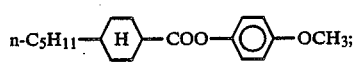
n-C₅H₁₁—⟨H⟩—COO—⌬—OCH₃;

-continued 16 wt % of

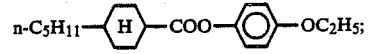
n-C₅H₁₁—⟨H⟩—COO—⌬—OC₂H₅;

16 wt % of

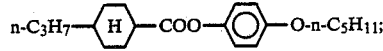
n-C₃H₇—⟨H⟩—COO—⌬—O-n-C₅H₁₁;

5 wt % of

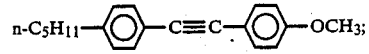
n-C₅H₁₁—⌬—C≡C—⌬—OCH₃;

6 wt % of

n-C₄H₉—⌬—C≡C—⌬—OC₂H₅;

3 wt % of

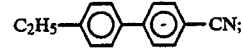
C₂H₅—⌬—⌬—CN;

7 wt % of

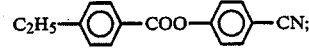
C₂H₅—⌬—COO—⌬—CN;

3 wt % of

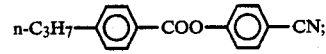
n-C₃H₇—⌬—COO—⌬—CN;

3 wt % of

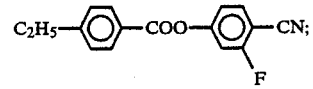
C₂H₅—⌬—COO—⌬(F)—CN;

3 wt % of

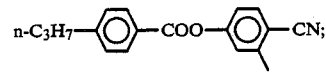
n-C₃H₇—⌬—COO—⌬(F)—CN;

2 wt % of

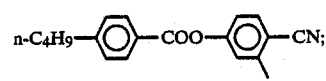
n-C₄H₉—⌬—COO—⌬(F)—CN;

and 3 wt % of

Figure 2:
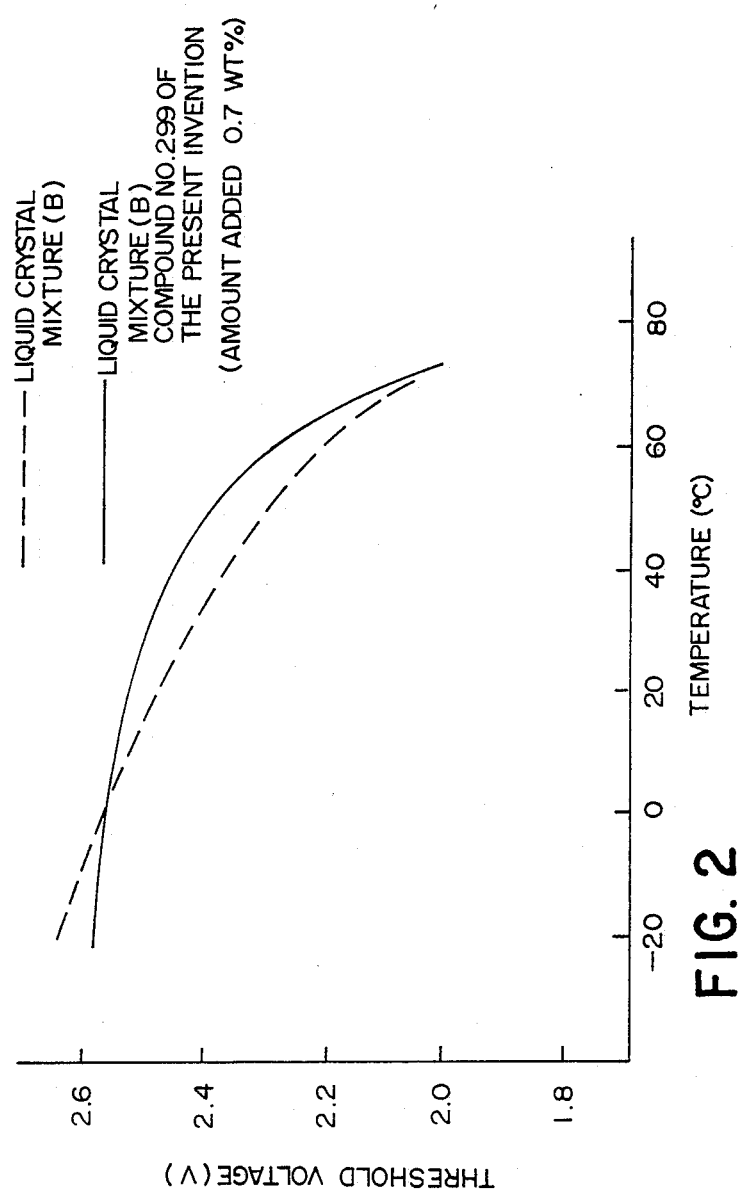
FIG. 2 is a graph showing the temperature dependency of threshold voltage of a chiral nematic liquid crystal composition which is prepared by adding 0.70 wt % of Optically Active Compound No. 299 (dextro rotation) of this invention to a mixed liquid crystal (B) commonly used as a nematic liquid crystal material at the present time.

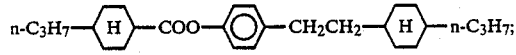
n-C₃H₇—⟨H⟩—COO—⌬—CH₂CH₂—⟨H⟩—n-C₃H₇;

FIG. 2 is a graph showing the temperature dependency of threshold voltage of each of a mixed liquid crystal (B) commonly used as a nematic liquid crystal material and of a chiral nematic liquid crystal composition as prepared by adding 0.70 wt % of Compound No. 299 (dextro rotation) of the general formula (I) of the present invention to the mixed liquid crystal (B). This chiral nematic liquid crystal composition has a pitch of 100 μm.

The mixed liquid crystal (B) is composed of:

13 wt % of n-C₃H₇—(H)—(O)—CN;

9 wt % of n-C₅H₁₁—(H)—COO—(O)—F;
                                  F 13 wt % of n-C₃H₇—(H)—(O)—OC₂H₅;

10 wt % of n-C₃H₇—(H)—COO—(O)—OC₂H₅;

2 wt % of C₂H₅—(H)—CH₂CH₂—(H)—COO—(O)—F;
                                              F 7 wt % of n-C₃H₇—(H)—CH₂CH₂—(H)—COO—(O)—F;
                                              F 5 wt % of n-C₄H₉—(H)—CH₂CH₂—(H)—COO—(O)—F;
                                              F 5 wt % of n-C₃H₇—(H)—(O)—COO—(O)—F;
                                      F 4 wt % of n-C₃H₇—(H)—(H)—COO—(O)—F;
                                      F 9 wt % of n-C₃H₇—(H)—CH₂CH₂—(H)—COO—(O)—F;
                                              F 4 wt % of C₂H₅—(H)—COO—(O)—CH₂CH₂—(H)—n-C₃H₇;

4 wt % of n-C₃H₇—(H)—COO—(O)—CH₂CH₂—(H)—n-C₃H₇;

8 wt % of n-C₃H₇—(H)—(O)—(O)—C₂H₅;

and 7 wt % of n-C₅H₁₁—(H)—(O)—(O)—C₂H₅.

It can be seen that the compounds of the general formula (I) have an effect of decreasing the temperature dependency of threshold voltage of a nematic liquid crystal composition when added thereto in a small amount.

The present invention is described in greater detail with reference to the following examples.

EXAMPLE 1

4.0 g (0.012 mol) of a compound having the formula (a):

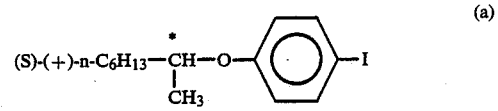

(a)

(wherein (S) indicates that the absolute arrangement with respect to a chiral center is sinister, and (+) indicates dextro rotation) was dissolved in 10 ml of diethylamine, and 24 mg (0.034 mmol) of bis(triphenylphosphine)palladium (II) chloride and 60 mg (0.31 mmol) of copper (II) iodide were added thereto. To the resulting mixture was dropped 2.1 g (0.012 mol) of p-n-pentylphenylacetylene while stirring the mixture at room temperature. After the dropwise addition was completed, the mixture was stirred for about 7 hours at room temperature. After the completion of the reaction, the reaction mixture was added to an excessive amount of hydro-chloric acid cooled with ice, and the resulting mixture was extracted with toluene and then washed with water and dried, and further recrystallized from ethanol and purified to obtain 3.4 g (0.0090 mol) of a compound having the following formula:

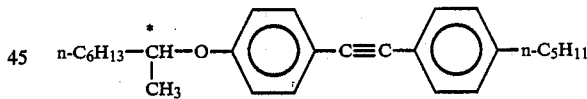

Yield: 75%.
$[\alpha]_D^{25} = +3.7$.
Transition Temperature: 38° C. (C→I).
The symbol "C" indicates a crystal phase, and "I", and isometric liquid phase.

EXAMPLE 2

The procedure of Example 1 was repeated with the exception that a compound having the formula (b):

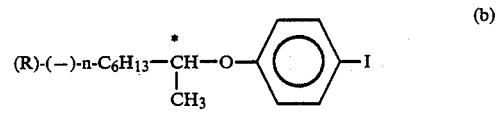

(b)

(wherein (R) indicates that the absolute arrangement with respect to a chiral center is rectus, and (−) indicates levo rotation) was used in place of the compound of the formula (a), to thereby obtain a compound having the following formula:

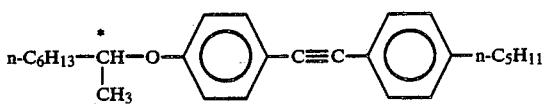

Yield: 69%.
[α]$_D^{25}$ = −2.4.
Transition temperature: 38° C. (C→I).

EXAMPLE 3

The procedure of Example 1 was repeated with the exception that 3.3 g (0.012 mol) of a compound having the formula:

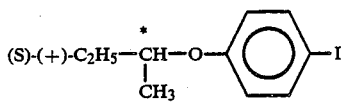

was used in place of the compound of the formula (a), and 1.6 g (0.012 mol) of p-methoxyphenylacetylene was used in place of the p-n-pentylphenylacetylene, to thereby obtain a compound having the formula:

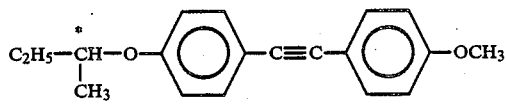

Yield: 58%.
[α]$_D^{25}$ = −21.0°.
Transition Temperature: 69° C. (C→I).

EXAMPLE 4

The procedure of Example 1 was repeated with the exception that 2.7 g (0.012 mol) of 4-(trans-4'-n-propylcyclohexyl)phenylacetylene was used in place of the p-n-pentylphenylacetylene, to thereby a compound having the following formula:

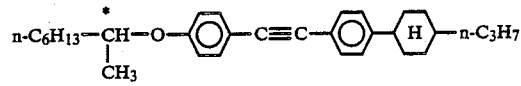

Yield: 65%.
[α]$_D^{25}$ = +1.80.
Transition Temperature: 75° C. (C→Ch), 117° C. (CH⇌I).

The symbol "C" indicates a crystal phase; "Ch", a colesteric phase; and "I", an isometric liquid phase.

The optically active compound of the present invention is a compound capable of decreasing the temperature dependency of threshold voltage of a nematic liquid crystal composition commonly used at the present time when added thereto in a small amount. Thus the optically active compound of the present invention is effective in preparation of liquid crystal material which is capable of effectively preventing the formation of the cross-talk phenomenon due to changes in the environmental temperature in high level multiplexing driving system.

What is claimed is:

1. In a nematic liquid crystal composition containing an additive to decrease the temperature dependency of threshold voltage of the composition, the improvement wherein the additive is an optically active tolan derivative represented by the formula,

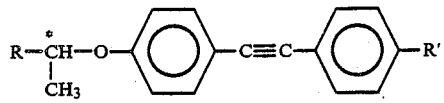

wherein R represents a straight chain alkyl group having 2 to 8 carbon atoms, R$^1$ represents a straight chain alkoxy group having 1 to 20 carbon atoms, and C* represents an asymmetrical carbon.

2. The optically active tolan derivative as in claim 1, wherein R is C$_2$H$_5$ and R' is O—CH$_3$.